United States Patent
Hess et al.

(10) Patent No.: US 6,403,837 B1
(45) Date of Patent: Jun. 11, 2002

(54) PROCESS FOR THE CATALYTIC PREPARATION OF ALDEHYDES FROM OLEFINS USING LIGAND MIXTURES

(75) Inventors: Dieter Hess, Marl; Dirk Roettger, Recklinghausen; Detlef Selent, Berlin; Armin Boerner, Rostock, all of (DE)

(73) Assignee: Oxeno Olefinchemie GmbH, Marl (DE)

( * ) Notice: Subject to any disclaimer, the term of this patent is extended or adjusted under 35 U.S.C. 154(b) by 0 days.

(21) Appl. No.: 09/708,624

(22) Filed: Nov. 9, 2000

(30) Foreign Application Priority Data

Nov. 12, 1999 (DE) .......................................... 199 54 510

(51) Int. Cl.[7] .............................................. C07C 45/50
(52) U.S. Cl. ...................................... 568/454; 568/451
(58) Field of Search .................................. 568/451, 454

(56) References Cited

U.S. PATENT DOCUMENTS

| | | | |
|---|---|---|---|
| 4,668,651 A | 5/1987 | Billig et al. | |
| 4,748,261 A | 5/1988 | Billig et al. | |
| 4,769,498 A | 9/1988 | Billig et al. | |
| 4,774,361 A | 9/1988 | Maher et al. | |
| 4,885,401 A | 12/1989 | Billig et al. | |
| 5,113,022 A | 5/1992 | Abatjoglou et al. | |
| 5,179,055 A | 1/1993 | Wink et al. | |
| 5,202,297 A | 4/1993 | Lorz et al. | |
| 5,235,113 A | 8/1993 | Sato et al. | |
| 5,254,741 A | 10/1993 | Lorz et al. | |
| 5,264,616 A | 11/1993 | Roeper et al. | |
| 5,312,996 A | 5/1994 | Packett | |
| 5,364,950 A | 11/1994 | Babin et al. | |
| 5,391,801 A | 2/1995 | Sato et al. | |
| 6,265,620 B1 * | 7/2001 | Urata et al. .................. | 568/454 |

FOREIGN PATENT DOCUMENTS

| | | |
|---|---|---|
| EP | 0 214 622 | 3/1987 |
| JP | 9-255610 | 9/1997 |
| JP | 9-268152 | 10/1997 |
| WO | WO 97/20795 | 6/1997 |
| WO | WO 98/43935 | 10/1998 |

OTHER PUBLICATIONS

Karlin, K.D., *Progress in Inorganic Chemistry*, Department of Chemistry, Johns Hopkins University, Baltimore, Maryland; vol. 48, An Interscience Publication (1999).

Cornils, B., Herrmann, W.A., *Aqueous–Phase Organometallic Catalysis Concepts and Applications*, Wiley–VCH, 1998.

Falbe, J., *New Syntheses with Carbon Monoxide*, Springer–Verlag, Berlin Heidelberg, New York 1980.

* cited by examiner

Primary Examiner—Sreeni Padmanabhan
(74) Attorney, Agent, or Firm—Oblon, Spivak, McClelland, Maier & Neustadt, P.C.

(57) ABSTRACT

A process for preparing aldehydes having from 4 to 25 carbon atoms by catalytic hydroformylation of the corresponding olefins, wherein the catalyst used comprises a metal of transition group 8 of the Periodic Table in the presence of a ligand A of the formula I

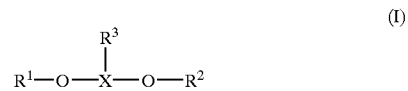

where X=As, Sb or P and $R^1, R^2, R^3$: are each a substituted or unsubstituted aliphatic, cycloaliphatic or aromatic hydrocarbon radical having from 1 to 50 carbon atoms, where two of the radicals $R^1$, $R^2$, $R^3$ can be covalently linked with the proviso that at least one of the hydrocarbon radicals $R^1$, $R^2$, $R^3$ contains a heteroatom selected from the group consisting of O, S, N, F, Cl, Be, I, Se and Te, and a ligand B of the formula II

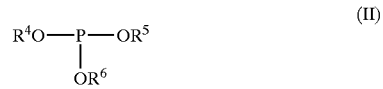

where $R^4$, $R^5$, $R^6$: are each a substituted or unsubstituted aliphatic, cycloaliphatic or aromatic hydrocarbon having from 1 to 50 carbon atoms, where two of the radicals R4, R5 and R6 can be covalently linked.

18 Claims, No Drawings

PROCESS FOR THE CATALYTIC PREPARATION OF ALDEHYDES FROM OLEFINS USING LIGAND MIXTURES

BACKGROUND OF THE INVENTION

1. Field of the invention

The present invention relates to a process for preparing aldehydes by hydroformylation of olefins or olefin mixtures in the presence of a catalyst comprising a metal of transition group 8, a phosphite ligand and a functionalized phosphonite ligand.

2. Background of the Invention

Aldehydes, in particular those having from 4 to 25 carbon atoms, can be prepared by catalytic hydroformylation of olefins having one less carbon atom (oxo process). The hydrogenation of these aldehydes gives alcohols which are used, for example, for preparing plasticizers or as detergents. Oxidation of the aldehydes gives carboxylic acids which can be used, for example, for preparing drying accelerators for surface coatings or as stabilizers for PVC.

The type of catalyst system and the optimum reaction conditions for the hydroformylation depends on the reactivity of the olefin used. A concise overview of hydroformylation, examples of catalysts and their fields of application, current industrial processes, etc., may be found in B. Cornils, W. A. Herrmann (Ed.), "Applied Homogeneous Catalysis with Organometallic Compounds", VCH, Weinheim, New-York, Basel, Cambridge, Tokyo, 1996, Vol. 1, pp. 29–104. The dependence of the reactivity of the olefins on their structure is described, for example, by J. Falbe, "New Syntheses with Carbon Monoxide", Springer-Verlag, Berlin, Heidelberg, N.Y., 1980, p. 95 ff. The differing reactivity of isomeric octenes is likewise known (B. L. Haymore, A. van Hasselt, R. Beck, Annals of the New York Acad. Sci., 415 (1983), pp. 159–175).

The various processes and catalysts make it possible to hydroformylate many olefins. A raw material which is of importance in terms of quantity is propene, from which n- and i-butyraldehyde are obtained.

Industrial olefin mixtures which are used as feedstocks for the oxo process often comprise olefins having a variety of structures with different degrees of branching, different positions of the double bond in the molecule and possibly also different numbers of carbon atoms. A typical example is raffinate I, which is a mixture of the $C_4$-olefins 1-butene, 2-butene and isobutene. This is particularly true of olefin mixtures which have been formed by dimerization, trimerization or further oligomerization of $C_2$–$C_5$-olefins or other readily available higher olefins or by cooligomerization of olefins. Examples of industrial olefin mixtures which can be hydroformylated to give the corresponding aldehyde mixtures are tripropene and tetrapropene and also dibutene, tributene and tetrabutene.

The products of the hydroformylation are determined by the structure of the starting olefins, the catalysts system and the reaction conditions. Under conditions under which no shift of the double bond in the olefin occurs, hereinafter referred to as nonisomerizing conditions, the formyl group is introduced at the place in the molecule where the double bond was located, which can result in two different products.

Thus, for example, the hydroformylation of 1-pentene can form hexanal and 2-methylpentanal. In the hydroformylation of 1-pentene under isomerizing conditions, under which a shift of the double bond in the olefin takes place in addition to the actual hydroformylation, 2-ethylbutanal would be expected as an additional product.

If alcohols for the preparation of detergents and plasticizers are sought as downstream products of the oxo aldehydes, predominantly linear aldehydes should be prepared in the oxo process. The products synthesized therefrom have particularly advantageous properties, e.g. low viscosities of the plasticizers prepared therefrom.

The abovementioned industrial olefin mixtures often contain only small proportions of olefins having a terminal double bond. To convert them into products in which more terminally hydroformylated olefin is present than in the original olefin mixture, the hydroformylation has to be carried out under isomerizing conditions. Processes suitable for this purpose are, for example, high-pressure hydroformylations using cobalt catalysts. However, these processes have the disadvantage that they form relatively large amounts of by-products, for example alkanes, acetals or ethers.

When using rhodium complexes as catalyst, the ligand also has a critical effect on the product composition of the aldehydes. Unmodified rhodium carbonyl complexes catalyze the hydroformylation of olefins having terminal and internal double bonds, which olefins may also be branched, to give aldehydes having a high degree of branching. The proportion of terminally hydroformylated olefin is significantly smaller than in the case of the cobalt-hydroformylated product.

In the presence of a ligand-modified catalyst system comprising rhodium and triorganophosphene, e.g. triphenylphosphene, α-olefins are terminally hydroformylated with high selectivity. Isomerization of the double bonds and/or hydroformylation of the internal double bonds hardly occur at all.

The hydroformylation of olefins having terminal double bonds in the presence of catalyst systems containing bulky phosphite ligands does not proceed satisfactorily at high conversions with high n/iso selectivity at the same time.

An overview of the influence of ligands on the activity and selectivity in hydroformylation may be found in the above-cited book by B. Cornils and W. A. Herrmann.

Compared to phosphene or phosphite ligands, the technical literature contains only few publications on the use of phosphorous diesters (hereinafter referred to as phosphonites) as ligands in hydroformylation reactions. JP-A Hei 9-268152, WO 98/43935 and JP-B Hei 9-255610 describe catalyst systems comprising rhodium, a triorganophosphonite ligand or a bidentate phosphonite ligand for the hydroformylation of acyclic or cyclic olefins or olefin mixtures. However, the hydroformylation of olefins having internal double bonds is not disclosed. Furthermore, there is no information on the structure of the products, in particular the ratio of internal to terminal hydroformylation.

WO 97/20795 describes a hydroformylation process in which metal organophosphites and sterically hindered organophosphorus ligands are used. This ligand combination is said to serve, by means of the different catalytic activity of the individual ligands, as an indicator for the activity of the total system. Phosphonite ligands are not described in WO 97/20795.

Furthermore, the use of polydentate polyphosphite ligands as constituents of hydroformylation catalysts is known from, for example, EP 0 214 622. Here too, various ligands are used at the same time. The effects of ligand mixtures on the linearity of the product are not described; in particular, a desired direction of the reaction to linear aldehydes is not disclosed.

SUMMARY OF THE INVENTION

It is therefore an object of the present invention to provide a process for the hydroformylation of olefins which enables branched, unbranched, terminal or internal olefins to be terminally hydroformylated in high yields and with high selectivities, i.e. it enables predominantly linear aldehydes to be prepared. It has surprisingly been found that the hydroformylation of olefins in the presence of catalysts comprising metals of transition group 8 together with phosphonites, arsenonites and stibenonites in the presence of organophosphites leads to linear, terminally hydroformylated products in high yields and with high selectivities.

The present invention accordingly provides a process for preparing aldehydes having from 4 to 25 carbon atoms by catalytic hydroformylation of the corresponding olefins, i.e., an olefin having 3 to 24 carbon atoms, wherein the catalyst comprises a metal of transition group 8 of the Periodic Table in the presence of a ligand A represented by formula I:

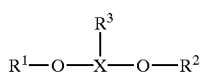
(I)

where

X is As, Sb or P; and $R^1$, $R^2$, $R^3$ are each a substituted or unsubstituted aliphatic, cycloaliphatic or aromatic hydrocarbon radical having from 1 to 50 carbon atoms, where two of the radicals $R^1$, $R^2$, $R^3$ can be covalently linked with the proviso that at least one of the hydrocarbon radicals $R^1$, $R^2$, $R^3$ contains a heteroatom selected from the group consisting of O, S, N, F, Cl, Br, I, Se and Te, and a ligand B represented by formula II:

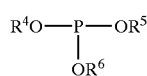
(II)

where $R^4$, $R^5$, $R^6$ are each a substituted or unsubstituted aliphatic or aromatic hydrocarbon having from 1 to 50 carbon atoms, where two of the radicals $R^4$, $R^5$ and $R^6$ can be covalently linked.

DETAILED DESCRIPTION OF THE INVENTION

The process of the invention makes it possible to prepare largely terminal aldehydes, i.e., products having a high n:iso ratio, at good total conversions. This constitutes a significant improvement on the known processes which either give good yields with moderate n:iso selectivities or moderate yields with good n:iso selectivities.

The olefin corresponding to an aldehyde is extended by one carbon atom by the process of the present invention, i.e. the corresponding olefin product has one less carbon atom than the aldehyde starting material.

The ligands A used in the process of the invention will hereinafter be referred to as heterofunctionalized phosphonites, arsenonites or stibenonites. For the purposes of the present invention, these heterofunctionalized phosphonites, arsenonites or stibenonites are compounds containing an atom of main group V of the Periodic Table (P, As, Sb) which has one free electron pair and two single bonds each to an oxygen atom and one single bond to a carbon atom. The formulae I, III, IV, V, VI and VII and also the examples in Table 1 show examples of ligands A useful in the process of the present invention.

In addition to the atom of main group 5, the ligands A contain at least one additional heteroatom having at least one free electron pair. The atom of main group 5 and the further heteroatom are positioned in the ligand A in such a way that a metal atom can be coordinated intramolecularly to both these atoms at the same time. This is the case when, for example, a phosphorus atom, a heteroatom and the intervening atoms can form a 4- to 15-membered ring, preferably a 4–9-membered ring, together with the coordinated metal atom.

These heteroatoms can be oxygen, sulfur, nitrogen, fluorine, chlorine, bromine, iodine, selenium or tellurium. These heteroatoms may be present in functional groups such as ethers, thioethers and tertiary amines and/or be part of a carbon chain or a ring. It is also possible for the ligands A to obtain more than one heteroatom which meets these requirements. The ligands A used according to the invention should be able to form a coordinate bond between heteroatom and metal which is less strong than that between the atom of main group V, i.e., P, As, Sb, and the metal.

In the technical literature, ligands which have a strong interaction with a metal together with a second, but distinctly weaker (labile) interaction are often referred to as hemilabile ligands (review articles: A. Bader, E. Linder, Coord. Chem. Rev. 1991, 108, 27–110; C. S. Slone, D. A. Weinberger, C. A. Mirkin, Prof. Inorg. Chem. 1999, 48, 233). In the case of some literature examples, the second, weaker interaction of the ligand, i.e. the heteroatom, with the metal has been able to be confirmed by means of X-ray structure analysis. In the case of the present heterofunctionalized ligands A, the coordination behavior is not known but it can be concluded from steric considerations that the metal is coordinated both to, for example, a phosphorus atom and to a heteroatom.

Suitable catalytically active metals are the metals of transition group 8 of the Periodic Table of the Elements, for example rhodium, cobalt, platinum or ruthenium.

In the process of the invention, the active catalyst complex for the hydroformylation is formed from a salt or a compound of the metal of transition group 8 of the Periodic Table (catalyst precursor), the ligands A and B, carbon monoxide and $H_2$, which advantageously occurs in situ during the hydroformylation. These components of the catalyst can be introduced into the process either together or separately; the catalyst complex is then formed by reaction with the synthesis gas. Customary catalyst precursors are, for example, octanoates, nonanoates or acetylacetonates. The molar ratio of metal to the ligands A and B is in each case from 1:1 to 1:100, preferably from 1:1 to 1:50. In practice, metal/ligand ratios of 1:5, 1:10 or 1:20 have been found to be useful. The concentration of the metal in the reaction mixture is in the range from 1 ppm to 1000 ppm, preferably in the range from 5 ppm to 300 ppm. The reaction temperatures in the process of the invention are in the range from 60° C. to 180° C., preferably from 90° C. to 150° C., and the pressures are 1–300 preferably 10–60 bar.

The ligands A used in the process of the invention may have the structures depicted by the formulae I, III, IV, V, VI and VII, shown below.

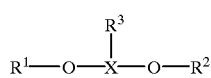

(I)

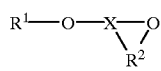

(III)

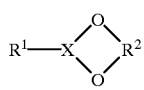

(IV)

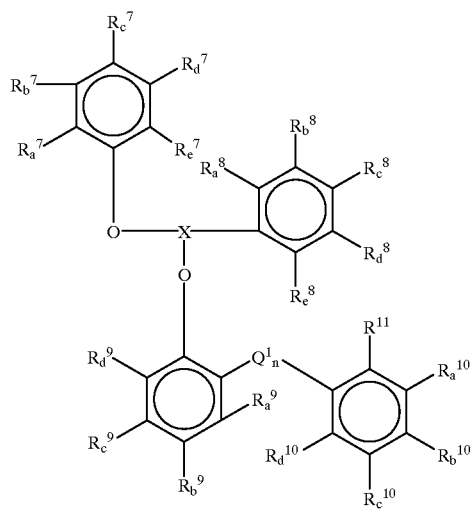

(V)

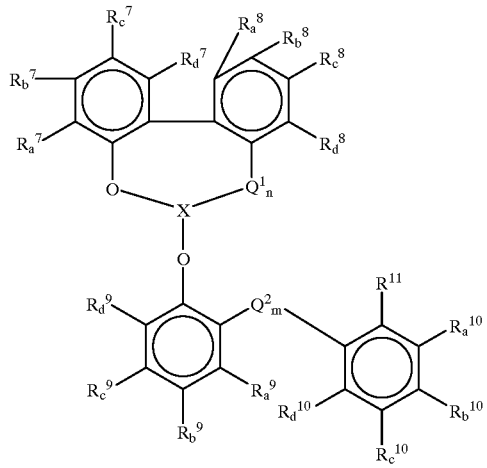

(VI)

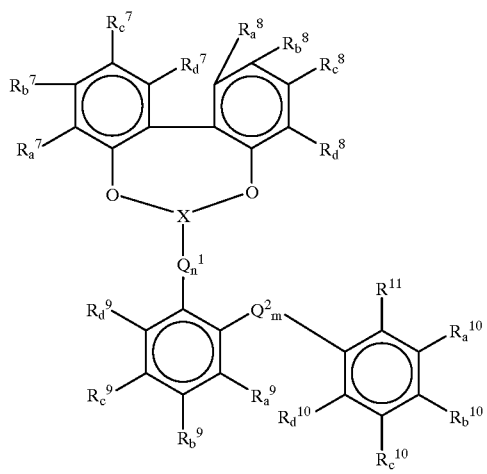

(VII)

In these formulae, the radicals $R^1$, $R^2$ and $R^3$ are each a substituted or unsubstituted, aliphatic, cycloaliphatic or aromatic hydrocarbon radical having from 1 to 50 carbon atoms, with the proviso that at least one of the hydrocarbon radicals $R^1$, $R^2$ or $R^3$ contains a heteroatom selected from the group consisting of O, S, N, F, Cl, Br, I, Se and Te. Two of the radicals $R^1$, $R^2$ and $R^3$ can be covalently linked to one another. The radical $R^2$ in the formulae III and IV is of course a divalent hydrocarbon radical.

The radicals $R^7_{a-e}$, $R^8_{a-e}$, $R^9_{a-d}$ and $R^{10}_{a-d}$ are each H, an aliphatic or aromatic hydrocarbon radical or an aliphatic or aromatic alkoxy group, each having from 1 to 25 carbon atoms, where the substituents with the indices a-e may in each case be identical or different.

Examples of ligands A having appropriate substitution patterns are shown in Table 1.

$R^{11}$ is $-O-R^{12}-CH_2-O-R^{12}$, $-COOR^{12}$, $-COOM$, $-SR^{12}$, $-NR^{12}R^{13}$, $-CH_2NR^{12}R^{13}$,

—CH$_2$CO$_2$M, —N=CR$^{12}$R$^{13}$, where R$^{12}$ and R$^{13}$ may be identical or different and are as defined for R$^7_a$, and M is H, Li, Na, K, NH$_4$, Examples of radicals R$^7_{a-e}$, R$^8_{a-e}$, R$^9_{a-d}$ and R$^{10}_{a-d}$ are H, t-butyl, methoxy, ethoxy, t-butoxy, isopropyl and t-amyl, X is a phosphorus, arsenic or antimony atom.

Q$^1$ and Q$^2$ are each a methylene radical or a group of the formula CR$^{14}$R$^{15}$ where R$^{14}$ and R$^{15}$ are identical or different and are as defined for R$^7_a$. The indices n and m are each 0 or 1.

Examples of ligands of type A which can be used in the process of the invention are:

TABLE 1

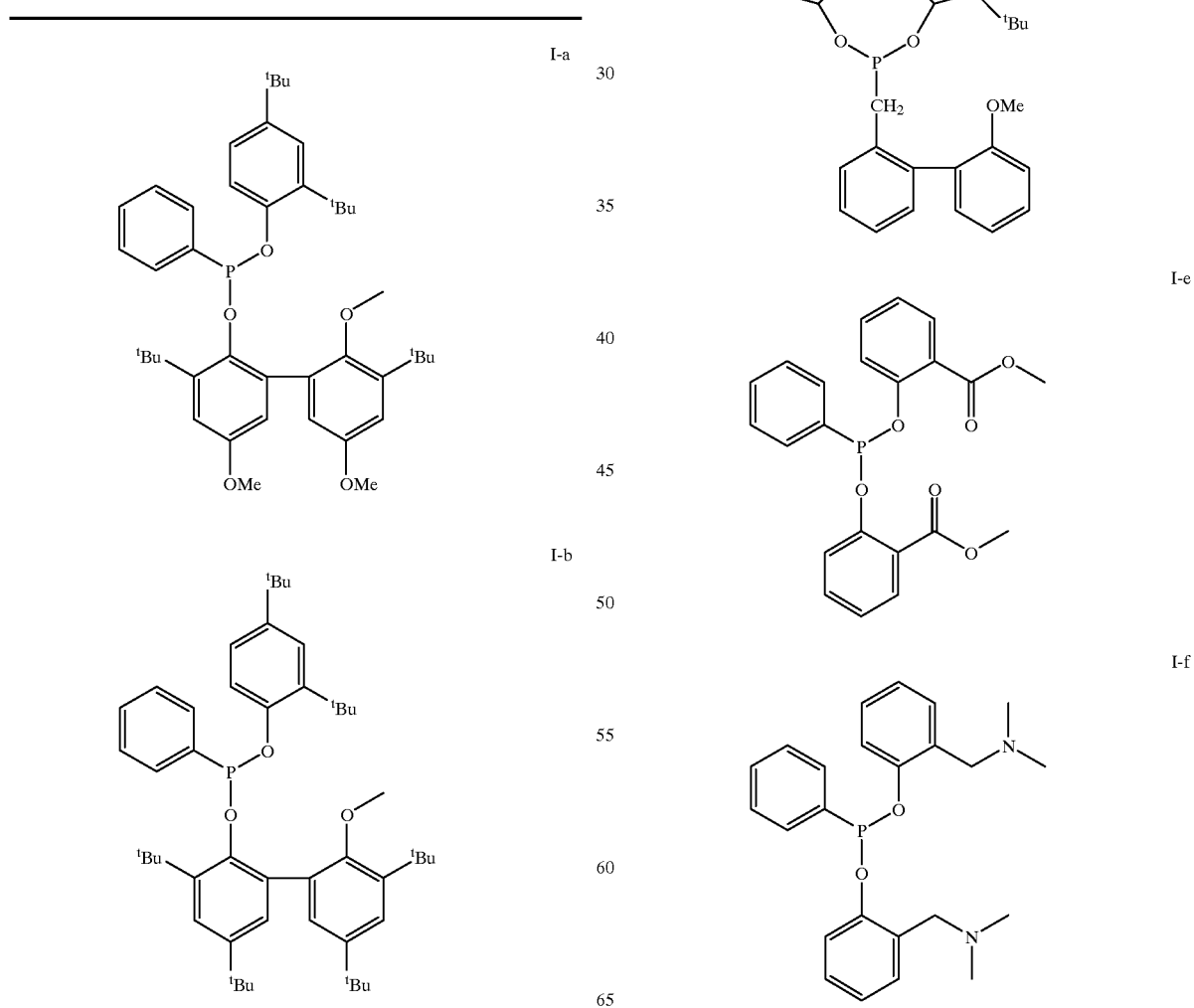

TABLE 1-continued

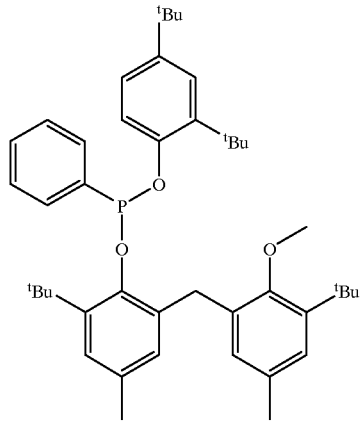

TABLE 1-continued
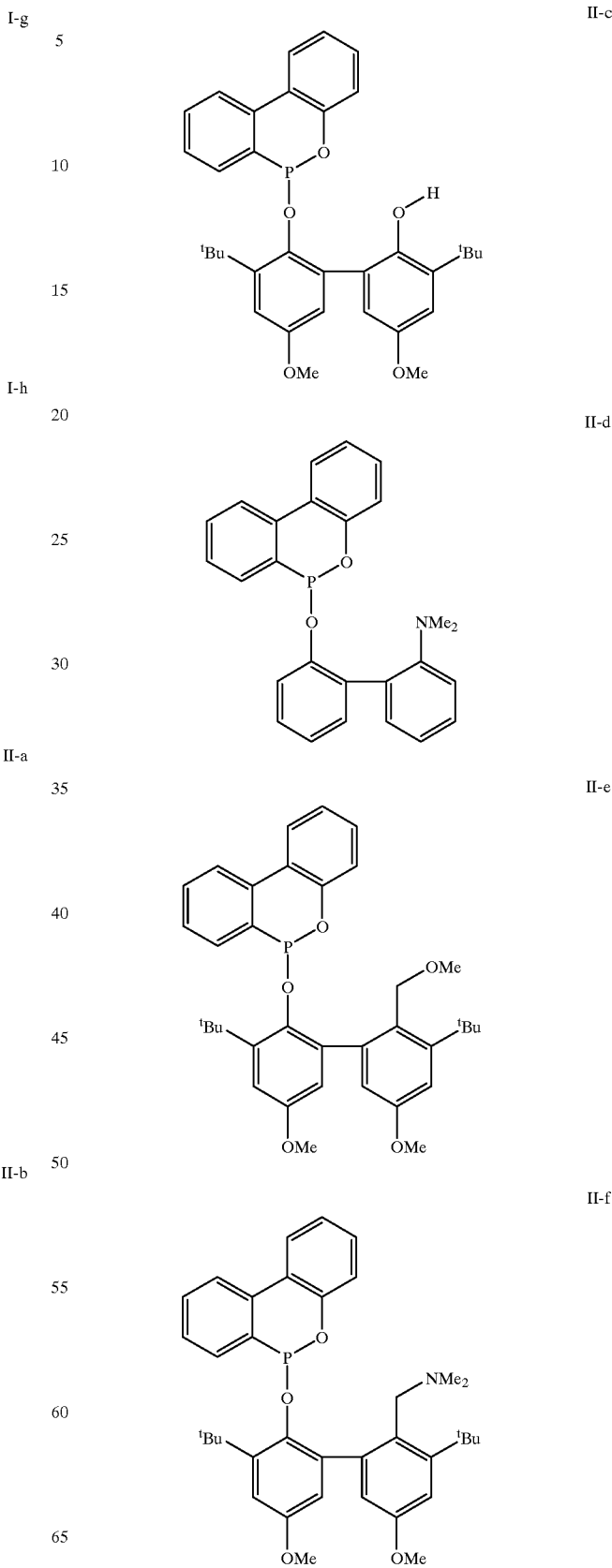

TABLE 1-continued
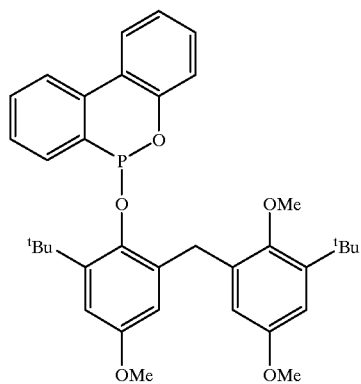
II-g
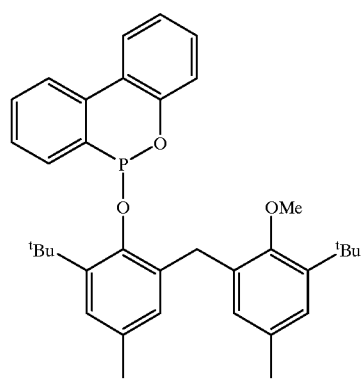
II-h
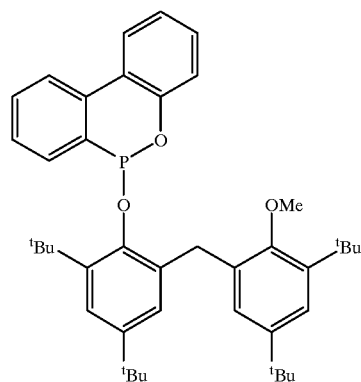
II-i
TABLE 1-continued
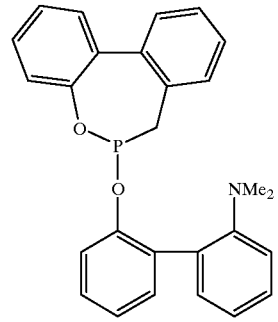
II-j
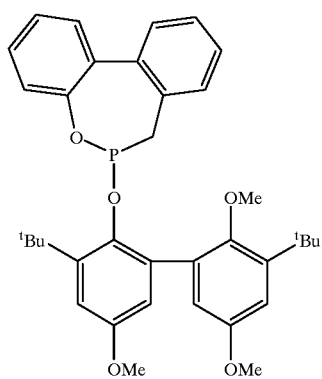
II-k
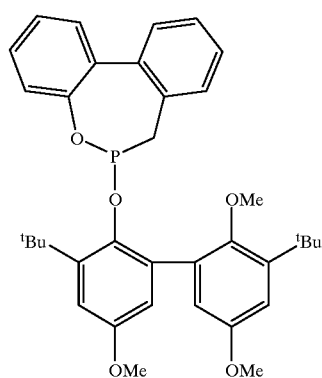
II-l
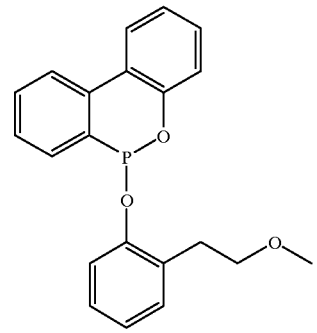
II-m TABLE 1-continued
II-n
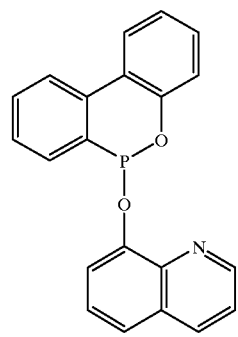
II-o
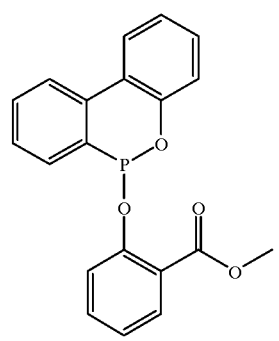
II-p
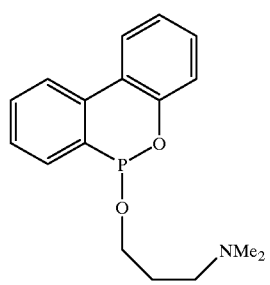
II-q
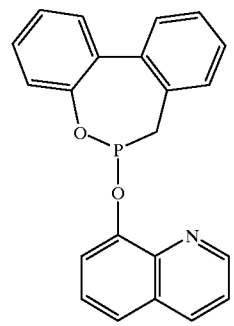
TABLE 1-continued
II-r
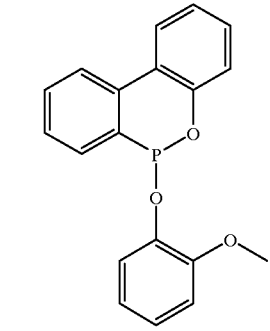
III-a
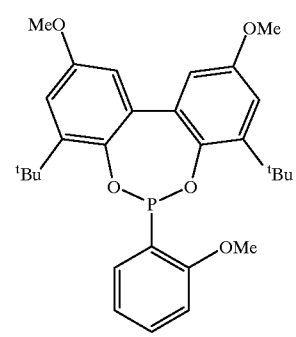
III-b
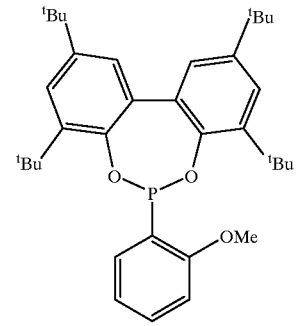
III-c
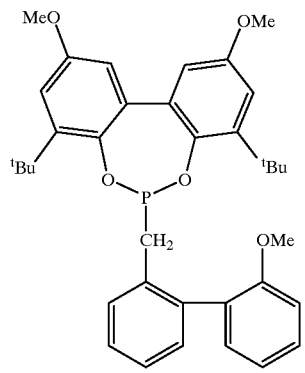

TABLE 1-continued

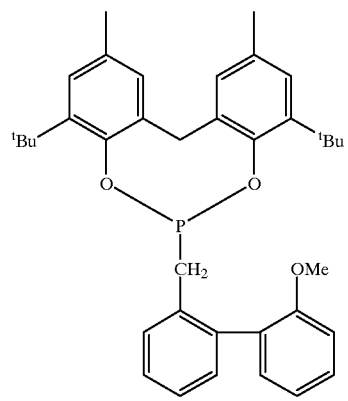

III-d

Ligands B which can be used in the process of the invention are:

R⁴O—P—OR⁵
    |
    OR⁶

(II)

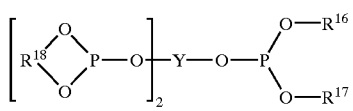

(VIII)

(IX)

(X)

(XI)

(XII)

(XIII)

The radicals or substituents are defined below:

$R^{16}$, $R^{17}$ are aliphatic or aromatic, substituted or unsubstituted hydrocarbon radicals having from 1 to 50 carbon atoms, where $R^{16}$ and $R^{17}$ may be identical or different, and $R^{18}$ is an aliphatic or aromatic, substituted or unsubstituted hydrocarbon radical having from 1 to 50 carbon atoms, and $R^{19}$, $R^{20}$ are aliphatic or aromatic, substituted or unsubstituted hydrocarbon radicals having from 1 to 50 carbon atoms, where $R^{19}$ and $R^{20}$ may be identical or different, $Q^3$ is $C(R^{21})_2$, O, S, $NR^{21}$, $Si(R^{21})_2$, CO, where $R^{21}$ is H, or a substituted or unsubstituted aliphatic or aromatic hydrocarbon radical having from 1 to 50 carbon atoms, x, y, p are integers from 0 to 5, Y is an aliphatic or aromatic, substituted or unsubstituted hydrocarbon radical having from 1 to 50 carbon atoms.

Examples of radicals Y, $R^{16}$, $R^{17}$ $R^{18}$ $R^{19}$ $R^{20}$ are methyl, ethyl, propyl, butyl, aryl, phenyl or naphthyl. These radicals can each be unsubstituted or substituted by, for example, nitro, carboxylate, carbonyl, cyano, amino, hydroxyl, sulfonyl, silyl, acyl, alkyl or aryl groups or halogens.

$R^{16}$ and $R^{17}$ are monovalent radicals while Y, $R^{18}$, $R^{19}$, $R^{20}$ and $Q^3$ are divalent radicals from the abovementioned groups.

Ligands of this type are known. Their preparation and use is described, for example, in U.S. Pat. Nos. 4,668,651; 4,748,261; 4,769,498; 4,774,361; 4,885,401; 5,113,022, 5,179,055; 5,202,297; 5,235,113; 5,254,741; 5,264,616; 5,312,996; 5,364,950 and 5,391,801.

As preferred ligands of type B, the following compounds may be used:

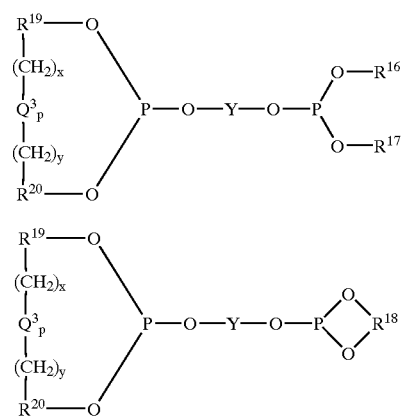

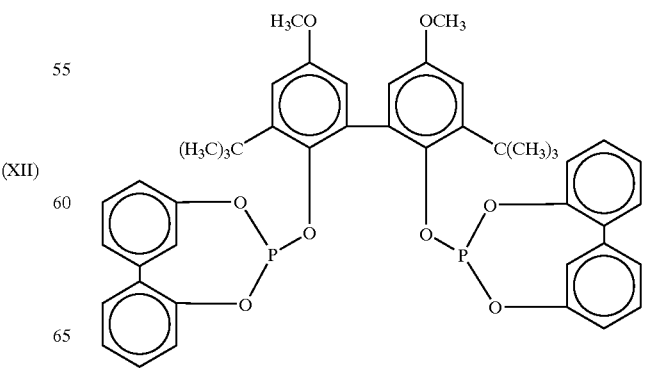

-continued

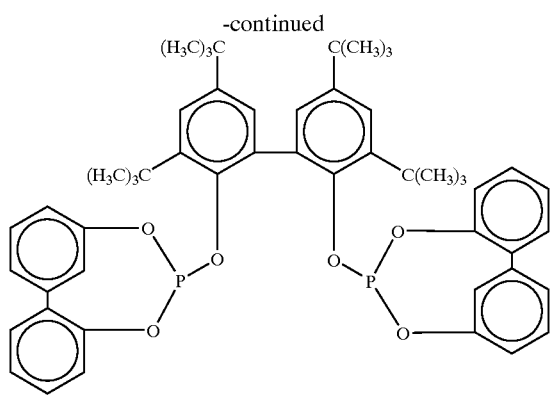

The catalyst, i.e., the metal of transition group 8 and ligands A and B, can be homogeneously dissolved in the hydroformylation mixture comprising starting material (olefin) and the product (aldehydes, alcohols, high boilers). If desired, it is possible to add an additional solvent such as alcohols or aldehydes, in this case again preferably the products of the hydroformylation.

The starting materials for a hydroformylation using the process of the invention are olefins or mixtures of olefins, in particular monoolefins having from 4 to 25, preferably from 4 to 16, particularly preferably from 4 to 8, carbon atoms and terminal or internal C—C double bonds, e.g., 1- or 2-pentene, 2-methyl-1-butane, 2-methyl-2-butene, 3-methyl-1-butane, 1-, 2- or 3-hexene, the $C_6$-olefin mixture obtained in the dimerization of propene (dipropene), heptenes, 2- or 3-methyl-1-hexene, octenes, 2-methylheptenes, 3-methylheptenes, 5-methyl-2-heptene, 6-methyl-2-heptene, 2-ethyl-1-hexene, the isomeric $C_8$-olefin mixture obtained in the dimerization of butenes (dibutene), nonenes, 2- or 3-methyloctenes, the $C_9$-olefin mixture obtained in the trimerization of propene (tripropene), decenes, 2-ethyl-1-octane, dodecenes, the $C_{12}$-olefin mixture obtained in the tetramerization of propene or the trimerization of butenes (tetrapropene or tributene), tetradecenes, hexadecenes, the $C_{16}$-olefin mixture obtained in the tetramerization of butenes (tetrabutene) and olefin mixtures prepared by cooligomerization of olefins having different numbers of carbon atoms (preferably from 2 to 4), if desired after fractional distillation to give fractions having the same or similar chain length. It is likewise possible to use olefins or olefin mixtures produced by the Fischer-Tropsch synthesis and also olefins which have been obtained by oligomerization of ethene or olefins which are obtainable via metathesis reactions. Preferred starting materials are $C_4$-, $C_8$-, $C_9$-, $C_{12}$- or $C_{16}$-olefin mixtures.

The process of the invention using the heterofunctionalized ligands makes it possible to hydroformylate α-olefins, branched, internal and internally branched olefins in high space-time yields. A notable aspect is the high yield of terminally hydroformylated olefin, even if only a small proportion of olefins having a terminal double bond was present in the starting material.

The ligand mixtures of ligands A and B used in the process of the present invention display a distinct synergistic effect and give good yields of products of high linearity, i. e. a good n:i ratio of the products, even when branched olefins are used as starting material.

EXAMPLES

Having generally described this invention, a further understanding can be obtained by reference to certain specific examples which are provided herein for purposes of illustration only and are not intended to be limiting unless otherwise specified.

By way of example, examples of various olefins were carried out using the following ligands:

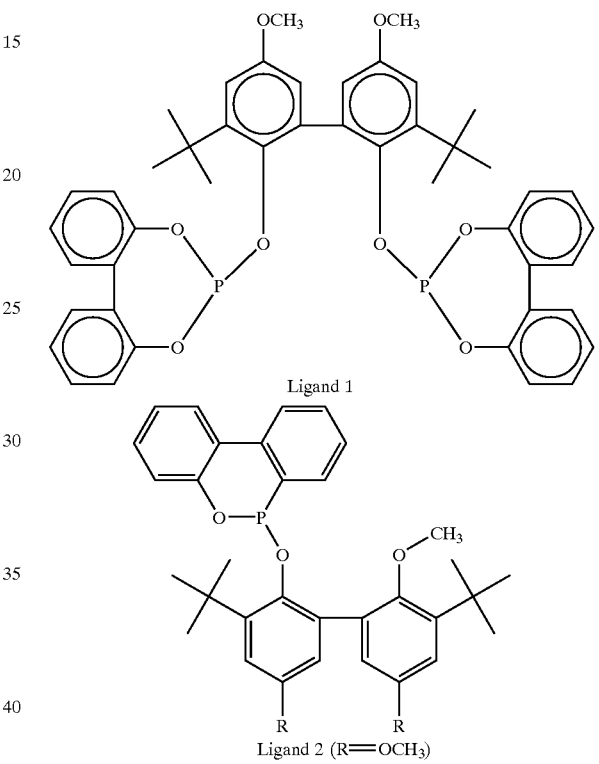

Ligand 1

Ligand 2 (R=OCH$_3$)

For comparison with the process of the invention, a mixture of ligand 1 with tris(2,4-di-tert-butylphenyl) phosphite (TDTBPP, ligand 3) was examined.

Ligand 1 corresponds to ligand type B; ligand 2 to ligand type A. All percentages are by weight unless otherwise indicated.

The experiments were carried out in 300 ml laboratory autoclaves from Berghof. For this purpose, 60 g of olefin+40 g of Texanol were placed in the autoclave. The ligand(s) and the Rh precursor were dissolved in 60 g of Texanol and introduced by means of a pressure pipette, at the start of the experiment. The catalyst precursor used was 0.135 g of rhodium nonanoate (corresponds to 200 mg/kg of Rh). Synthesis gas (50% by volume of H2, 50% by volume of CO) was metered in via a sparging stirrer at such a rate that the pressure was kept constant. The reaction time was 8 h, the stirrer speed was 1000 revolutions per minute. The experiments were carried out at 140° C. and 20 bar.

Experiment 1

In an experiment using 200 ppm of Rh, ligand 1 (P:Rh=10:1) and 60 g of 2,4,4-trimethyl-2-pentene, a branched olefin having an internal double bond, only 1.6% of 3,5,5-trimethylhexanal was formed after 8 hours at 140° C. and 20 bar.

Experiment 2

In an experiment using 200 ppm of Rh, ligand 1 (P:Rh=10: 1) and 60 g of 2,4,4-trimethyl-1-pentene, a conversion to 3,5,5-trimethylhexanal of 76.5% was achieved after 8 hours at 140° C. and 20 bar.

Experiment 3

In an experiment using 200 ppm of Rh, ligand 1 (P:Rh=10:1) and 60 g of a mixture of unbranched octenes containing about 3.3% of 1-octene, a conversion to nonanal of 91.9% is achieved after 8 hours at 140° C. and 20 bar. The ligand thus gives an excellent selectivity to 1-nonanal.

Experiment 4

In an experiment using 200 ppm of Rh, ligand 2 (P:Rh=10:1) and 60 g of 2,4,4-trimethyl-2-pentene, a conversion to 3,5,5-trimethylhexanal of only 11.3% is achieved, but the product mixture contains 63.8% of 2,4,4-trimethyl-1-pentene.

Experiment 5

In an experiment using 200 ppm of Rh, ligand 2 (P:Rh=10:1) and 60 g of 2,4,4-trimethyl-1-pentene, a conversion to 3,5,5-trimethylhexanal of 46.4% is achieved.

Experiment 6

In an experiment using 200 ppm of Rh, ligand 2 (P:Rh=10:1) and 60 g a mixture of unbranched octenes containing about 3.3% of 1-octene, a conversion to nonanal of 27.7% and a total conversion of about 70% are achieved at 140° C. and 20 bar.

Experiment 7

Use of 200 ppm of Rh, the ligand 1 (P:Rh ratio=10:1) and 60 g of di-n-butene as olefin gives a ratio of 3.53 in the experimental product at a conversion of 40% after a reaction time of 8 hours.

Experiment 8

Use of 200 ppm of Rh, the ligand 2 (P:Rh ratio=10:1) and 60 g of di-n-butene as olefin gives an n/iso ratio of 0.7 in the experimental product at a conversion of 30% after a reaction time of 8 hours.

Experiment 9

Use of 200 ppm of Rh, the ligand 1 (P:Rh ratio=2:1) and 60 g of di-n-butene as olefin gives an n/iso ratio of 0.96 in the experimental product at a conversion of 70% after a reaction time of 8 hours.

Experiment 10

Use of 200 ppm of Rh, a mixture of ligand 1 and ligand 2 (in each case P:Rh=5:1) and 60 g of di-n-butene as olefin gives an n/iso ratio of 1.83 in the experimental product at a conversion of 73% after a reaction time of 8 hours. The mixture surprisingly gave a conversion which is significantly higher than the conversion which can be achieved using the individual ligands while the n/i ratio was still high.

Experiment 11

Use of 200 ppm of Rh, a mixture of ligand 1 (P:Rh=5:1) and ligand 2 (P:Rh=10:1) and 60 g of di-n-butene as olefin gives an n/iso ratio of 1.29 in the experimental product at a conversion of 83% after a reaction time of 8 hours. The mixture thus gives both a good n/i ratio and an even higher conversion than in Experiment 10.

The mixtures of ligands 1 and 2 thus display a distinct synergistic effect.

Experiments 12 to 14

Comparative Examples

Experiment 12

Use of 200 ppm of Rh, a mixture of ligand 1 and ligand 3 (in each case P:Rh=10:1) and 60 g of di-n-butene as olefin gives an n/iso ratio of 3.41 in the experimental product at a conversion of 37% after a reaction time of 8 hours.

Experiment 13

Use of 200 ppm of Rh, a mixture of ligand 1 (P:Rh=5:1) and ligand 3 (P:Rh=10:1) and 60 g of di-n-butene as olefin gives an n-iso ratio of 3.61 in the experimental product at a conversion of only 40% after a reaction time of 8 hours.

Experiment 14

Use of 200 ppm of Rh, a mixture of ligand 1 (P:Rh=2:1) and ligand 3 (P:Rh=10:1) and 60 g of di-n-butene as olefin gives an n/iso ratio of 0.71 in the experimental product at a conversion of 93% after a reaction time of 8 hours. Mixtures of ligand 1 and ligand 3 thus behave additively. A synergistic effect on the conversion as in the case of the mixture of ligand 1 and ligand 2 used according to the invention is not observed.

Table 3 provides a summary of the experimental results.

| Experiment | Ligand P: | Rh | Starting olefin | Conversion % | Selectivity n:i |
|---|---|---|---|---|---|
| 1 | 1, | 10:1 | 2,4,4-trimethyl-2-pentene | 1.6 | |
| 2 | 1, | 10:1 | 2,4,4-trimethyl-1-pentene | 76.5 | |
| 3 | 1, | 10:1 | n-octene | 91.9 | |
| 4 | 2, | 10:1 | 2,4,4-trimethyl-2-pentene | 11.3 | |
| 5 | 2, | 10:1 | 2,4,4-trimethyl-2-pentene | 46.4 | |
| 6 | 2, | 10:1 | n-octene | 70.0 | 0.65 |
| 7 | 1, | 10:1 | di-n-butene | 40 | 3.53 |
| 8 | 2, | 10:1 | di-n-butene | 30 | 0.7 |
| 9 | 1, | 2:1 | di-n-butene | 70 | 0.96 |
| 10 | 1, 5:1 + 2, | 5:1 | di-n-butene | 73 | 1.83 |
| 11 | 1, 5:1 + 2, | 10:1 | di-n-butene | 83 | 1.29 |
| 12 | 1, 10:1 + 3, | 10:1 | di-n-butene | 37 | 3.41 |
| 13 | 1, 5:1 + 3, | 10:1 | di-n-butene | 40 | 3.61 |
| 14 | 1, 2:1 + 3, | 10:1 | di-n-butene | 93 | 0.71 |

Obviously, numerous modifications and variations of the present invention are possible in light of the above teachings. It is therefore to be understood that within the scope of the appended claims, the invention may be practiced otherwise than as specifically described herein.

This application is based on German Patent Application Serial No. 199 54 510.3, filed on Nov. 12, 1999, the entire contents of which is incorporated herein by reference.

What is claimed is:

1. A process for preparing aldehydes having from 4 to 25 carbon atoms by catalytic hydroformylation of the corresponding olefins, comprising:

hydroformylating an olefin having from 3 to 24 carbon atoms in the presence of a catalyst, wherein the catalyst comprises a metal of transition group 8 of the Periodic Table in the presence of a ligand A represented by formula I:

(I)

wherein

X is As, Sb or P; and $R^1$, $R^2$, $R^3$ are each a substituted or unsubstituted aliphatic, cycloaliphatic or aromatic hydrocarbon radical having from 1 to 50 carbon atoms, where two of the radicals $R^1$, $R^2$, $R^3$ can be covalently linked with the proviso that at least one of the hydrocarbon radicals $R^1$, $R^2$, $R^3$ contains a heteroatom selected from the group consisting of O, S, N, F, Cl, Br, I, Se and Te, and a ligand B represented by formula II:

$$R^4O-P(OR^6)-OR^5 \quad (II)$$

wherein $R^4$, $R^5$, $R^6$ are each a substituted or unsubstituted aliphatic or aromatic hydrocarbon having from 1 to 50 carbon atoms, where two of the radicals $R^4$, $R^5$ and $R^6$ can be covalently linked.

2. The process of claim 1, wherein the ligand A is represented by formula III:

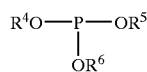

(III)

wherein

X is As, Sb or P; and $R^1$, $R^2$ are substituted or unsubstituted, aliphatic, cycloaliphatic or aromatic hydrocarbon radicals having from 1 to 50 carbon atoms, with the proviso that $R^1$ or $R^2$ contains a heteroatom selected from the group consisting of O, S, N, F, Cl, Br, I, Se and Te.

3. The process of claim 1, wherein the ligand A is represented by formula IV:

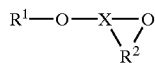

(IV)

wherein

X is As, Sb or P; and $R^1$, $R^2$ are substituted or unsubstituted, aliphatic, cycloaliphatic or aromatic hydrocarbon radicals having from 1 to 50 carbon atoms, with the proviso that $R^1$ or $R^2$ contains a heteroatom selected from the group consisting of O, S, N, F, Cl, Br, I, Se and Te.

4. The process of claim 1, wherein the ligand A is represented by formula V:

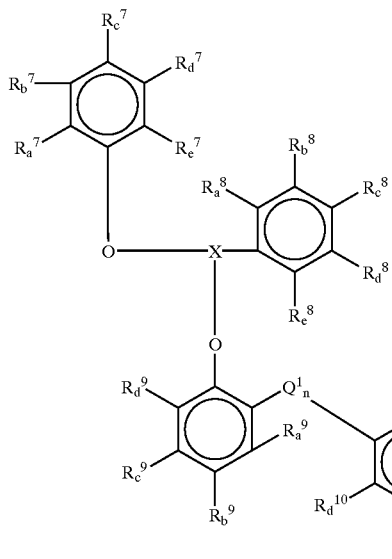

(V)

wherein

X is As, Sb or P;

$R^7_{a-e}$, $R^8_{a-e}$, $R^9_{a-d}$ and $R^{10}_{a-d}$ are H, aliphatic or aromatic hydrocarbon radicals, aliphatic or aromatic alkoxy groups, each having from 1 to 25 carbon atoms, where the substituents with the indices a-e may in each case be identical or different;

$R^{11}$ is $-O-R^{12}$, $-CH_2-O-R^{12}$, $-COOR^{12}$, $-COOM$, $-SR^{12}$, $-NR^{12}R^{13}$, $-CH_2NR^{12}R_{13}$, $-N=CR^{12}R^{13}$, $-CH_2COOM$, where $R^{12}$ and $R^{13}$ may be identical or different and are as defined for $R^7_a$ and M is H, Li, Na, K, $NH_4$, $Q^1$ is $CR^{14}R^{15}$, where $R^{14}$ and $R^{15}$ may be identical or different and are as defined for $R^7_a$; and n is 0 or 1.

5. The process of claim 1, wherein the ligand A used is represented by formula VI:

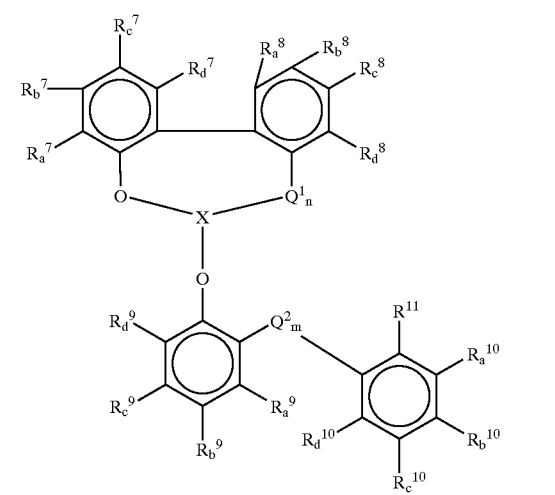

(VI)

wherein
X is As, Sb or P;
$R^7_{a-d}$, $R^8_{a-d}$, $R^9_{a-d}$ and $R^{10}_{a-d}$ are H, aliphatic or aromatic hydrocarbon radicals, aliphatic or aromatic alkoxy groups, each having from 1 to 25 carbon atoms, where the substituents with the indices a-d may in each case be identical or different;
$R^{11}$ is $-O-R^{12}$, $-CH_2-O-R^{12}$, $-COOR^{12}$, $-COOM$, $-SR^{12}$, $-NR^{12}R^{13}$, $-CH_2NR^{12}R^{13}$, $-N=CR^{12}R_{13}$, $-CH_2COOM$;
$Q^1$, $Q^2$ are $CR^{14}R^{15}$ where $R^{12}$, $R^{13}$, $R^{14}$ and $R^{15}$ may be identical or different and are as defined for $R^7_a$ and M is H, Li, Na, K, $NH_4$; and
n, m is 0 or 1.

6. The process of claim 1, wherein the ligand A is represented by formula VII:

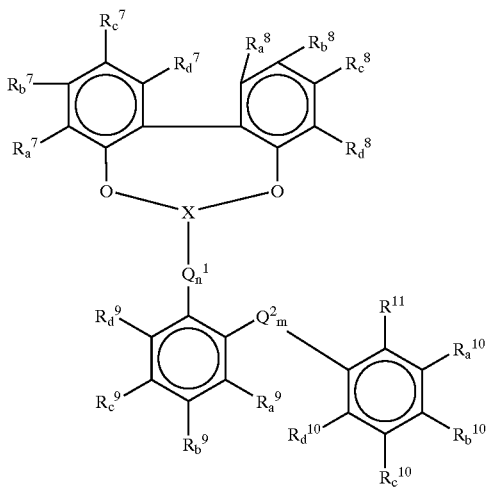

(VII)

wherein
X is As, Sb or P;
$R^7_{a-d}$, $R^8_{a-d}$, $R^9_{a-d}$ and $R^{10}_{a-d}$ are H, aliphatic or aromatic hydrocarbon radicals, aliphatic or aromatic alkoxy groups, each having from 1 to 25 carbon atoms, where the substituents with the indices a-d may in each case be identical or different;
$R^{11}$ is $-O-R^{12}$, $-CH_2-O-R^{12}$, $-COOR^{12}$, $-COOM$, $-SR^{12}$, $-NR^{12}R^{13}$, $-CH_2NR^{12}R^{13}$, $-N=CR^{12}R^{13}$, $-CH_2CO_2M$,
$Q^1$, $Q^2$ are $CR^{14}R^{15}$ where $R^{12}$, $R^{13}$, $R^{14}$ and $R^{15}$ may be identical or different and are as defined for $R^7_a$ and M is H, Na, K and
n, m is 0 or 1.

7. The process of claim 1, wherein the ligand B is represented by formula VIII:

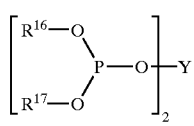

(VIII)

wherein
$R^{16}$, $R^{17}$ are aliphatic or aromatic, substituted or unsubstituted hydrocarbon radicals having from 1 to 50 carbon atoms, where $R^{16}$ and $R^{17}$ may be identical or different; and Y is an aliphatic or aromatic, substituted or unsubstituted hydrocarbon radical having from 1 to 50 carbon atoms.

8. The process of claim 1, wherein the ligand B is represented by the formula IX:

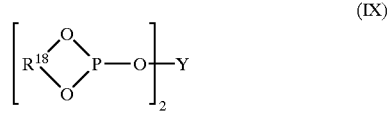

(IX)

wherein
$R^{18}$ is an aliphatic or aromatic, substituted or unsubstituted hydrocarbon radical having from 1 to 50 carbon atoms; and
Y is an aliphatic or aromatic, substituted or unsubstituted hydrocarbon radical having from 1 to 50 carbon atoms.

9. The process of claim 1, wherein the ligand B is represented by formula X:

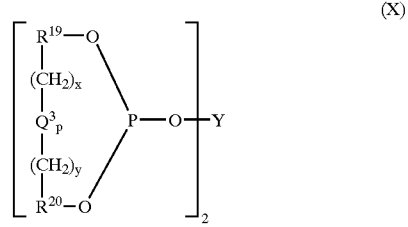

(X)

wherein
$R^{19}$, $R^{20}$ are aliphatic or aromatic, substituted or unsubstituted hydrocarbon radicals having from 1 to 50 carbon atoms, where $R^{19}$ and $R^{20}$ may be identical or different;
$Q^3$ is $C(R^{21})_2$, O, S, $NR^{21}$, $Si(R^{21})_2$, CO, where $R^{21}$ is H or a substituted or unsubstituted aliphatic or aromatic hydrocarbon radical having from 1 to 50 carbon atoms;
Y is an aliphatic or aromatic, substituted or unsubstituted hydrocarbon radical having from 1 to 50 carbon atoms; and
x, y, p are from 0 to 5.

10. The process of claim 1, wherein the ligand B is represented by formula XI:

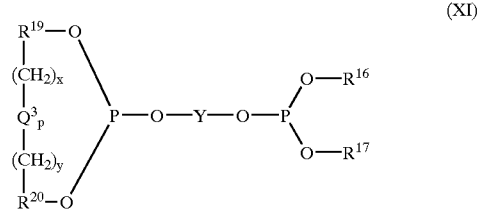

(XI)

wherein
$R^{16}$, $R^{17}$ are aliphatic or aromatic, substituted or unsubstituted hydrocarbon radicals having from 1 to 50 carbon atoms, where $R^{16}$ and $R^{17}$ may be identical or different,
$R^{19}$, $R^{20}$ are aliphatic or aromatic, substituted or unsubstituted hydrocarbon radicals having from 1 to 50 carbon atoms, where $R^{19}$ and $R^{20}$ may be identical or different,
$Q^3$ is $C(R^{21})_2$, O, S, $NR^{21}$, $Si(R^{21})_2$, C, where $R^{21}$ is H or a substituted or unsubstituted aliphatic or aromatic hydrocarbon radical having from 1 to 50 carbon atoms, x, y, p are from 0 to 5 and Y is an aliphatic or aromatic, substituted or unsubstituted hydrocarbon radical having from 1 to 50 carbon atoms.

11. The process of claim 1, wherein the ligand B is represented by formula XII:

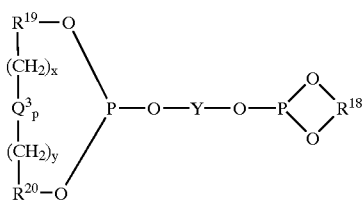

wherein $R^{18}$, $R^{19}$, $R^{20}$ is an aliphatic or aromatic, substituted or unsubstituted hydrocarbon radicals having from 1 to 50 carbon atoms, where $R^{18}$, $R^{19}$ and $R^{20}$ may be identical or different, $Q^3$ is $C(R^{21})_2$, O, S, $NR^{21}$, $Si(R^{21})_2$, CO, where $R^{21}$ is H or a substituted or unsubstituted aliphatic or aromatic hydrocarbon radical having from 1 to 50 carbon atoms, x, y, p are from 0 to 5 and Y is an aliphatic or aromatic, substituted or unsubstituted hydrocarbon radical having from 1 to 50 carbon atoms.

12. The process of claim 1, wherein the ligand B is represented by formula XIII:

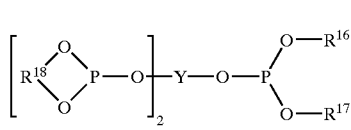

wherein $R^{16}$, $R^{17}$, $R^{18}$ are aliphatic or aromatic, substituted or unsubstituted hydrocarbon radicals having from 1 to 50 carbon atoms, where $R^{16}$, $R^{17}$ and $R^{18}$ may be identical or different; and Y is an aliphatic or aromatic, substituted or unsubstituted hydrocarbon radical having from 1 to 50 carbon atoms.

13. The process according to claim 1 wherein the olefin is an olefin having from 4 to 25 carbon atoms or a mixture of olefins having from 4 to 25 carbon atoms and having terminal or internal double bonds.

14. The process of claim 13, wherein the ligand A is represented by formula III:

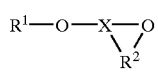

wherein

X is As, Sb or P; and $R^1$, $R^2$ are substituted or unsubstituted, aliphatic, cycloaliphatic or aromatic hydrocarbon radicals having from 1 to 50 carbon atoms, with the proviso that $R^1$ or $R^2$ contains a heteroatom selected from the group consisting of O, S, N, F, Cl, Br, I, Se and Te.

15. The process of claim 13, wherein the ligand A is represented by formula IV:

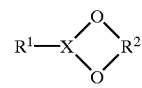

wherein

X is As, Sb or P; and $R^1$, $R^2$ are substituted or unsubstituted, aliphatic, cycloaliphatic or aromatic hydrocarbon radicals having from 1 to 50 carbon atoms, with the proviso that $R^1$ or $R^2$ contains a heteroatom selected from the group consisting of O, S, N, F, Cl, Br, I, Se and Te.

16. The process of claim 13, wherein the ligand B is represented by formula VIII:

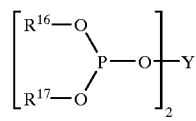

wherein $R^{16}$, $R^{17}$ are aliphatic or aromatic, substituted or unsubstituted hydrocarbon radicals having from 1 to 50 carbon atoms, where $R^{16}$ and $R^{17}$ may be identical or different; and Y is an aliphatic or aromatic, substituted or unsubstituted hydrocarbon radical having from 1 to 50 carbon atoms.

17. The process of claim 13, wherein the ligand B is represented by the formula IX:

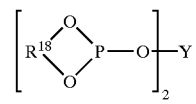

$R^{18}$ are aliphatic or aromatic, substituted or unsubstituted hydrocarbon radical having from 1 to 50 carbon atoms; and Y is an aliphatic or aromatic, substituted or unsubstituted hydrocarbon radical having from 1 to 50 carbon atoms.

18. The process of claim 14, wherein the ligand B is represented by the formula IX:

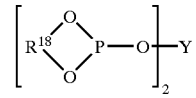

$R^{18}$ are aliphatic or aromatic, substituted or unsubstituted hydrocarbon radical having from 1 to 50 carbon atoms; and Y is an aliphatic or aromatic, substituted or unsubstituted hydrocarbon radical having from 1 to 50 carbon atoms.

* * * * *